United States Patent
Chow

(10) Patent No.: US 6,496,984 B1
(45) Date of Patent: Dec. 24, 2002

(54) CMC JOINT SPLINT

(76) Inventor: James C. Y. Chow, 4121 Veterans Memorial Dr., Mount Vernon, IL (US) 62864

( * ) Notice: Subject to any disclaimer, the term of this patent is extended or adjusted under 35 U.S.C. 154(b) by 0 days.

(21) Appl. No.: 10/032,669

(22) Filed: Oct. 25, 2001

(51) Int. Cl.$^7$ ................................................ A41D 13/08
(52) U.S. Cl. ................................................ 2/16; 602/21
(58) Field of Search ...................... 2/16, 20, 21, 161.1, 2/161.5, 161.6, 161.7, 160, 163; 128/878, 879, 880; 602/5, 6, 9, 21, 22

(56) References Cited

U.S. PATENT DOCUMENTS

| | | | |
|---|---|---|---|
| 4,709,694 A | * 12/1987 | O'Connell | 2/167 |
| 4,840,168 A | * 6/1989 | Lonardo | 602/22 |
| 5,771,901 A | * 6/1998 | O'Brien | 128/878 |
| 6,146,347 A | * 11/2000 | Porrata | 128/879 |

* cited by examiner

*Primary Examiner*—Gary L Welch
(74) *Attorney, Agent, or Firm*—Polster, Lieder, Woodruff & Lucchesi, L.C.

(57) ABSTRACT

A CMC splint (10) supporting the thumb (T) and index finger (I) of a person's hand in a spread apart, separated position. A sleeve (12) having an open end (14) is sized to fit over the person's arm (A) and extend up the person's arm a distance between their wrist and elbow. The other end (16) of the sleeve is closed, but has openings (18) therein through which the thumb and fingers of the person's hand extend. A stiffening member (20) contained in the sleeve at its closed end keeps the person's thumb and index finger spread apart from each other in a spaced relationship to protect the CMC joint of the hand and allow the joint to heal. The stiffening member comprises a curved pad extending from the base of the index finger, about a curved web portion of the hand separating the index finger and the thumb, and along an inside surface of the thumb a distance above the base of the thumb.

10 Claims, 2 Drawing Sheets

CMC JOINT SPLINT

CROSS REFERENCE TO RELATED APPLICATIONS

STATEMENT REGARDING FEDERALLY SPONSORED RESEARCH OR DEVELOPMENT

BACKGROUND OF THE INVENTION

This invention relates to orthopedic devices; and more to particularly, to a joint splint for use by those suffering from carpometacarpal (CMC) joint pain.

As a person ages, they sometimes begin to suffer from osteoarthritis which is a degenerative condition. This can result in a painful condition in which it becomes difficult for the person to move their thumb without experiencing an excruciating pain. While this condition can be surgically treated, a more conservative, non-invasive approach is to restrict movement of the thumb. One way of achieving this is to have the patient wear an orthotic device or appliance which effectively immobilizes the thumb, while preferably not unduly effecting the person's use of the rest of their hand.

CMC splints are known in the arts. See, for example, U.S. Pat. No. 5,561,856. There are a number of problems with conventional splints. First, they are not comfortable to wear. Often, the material from which they are made is too thick or too bulky. A thick material causes sweating, and the bulkiness of the material makes it difficult for the splint to be worn underneath a shirt or blouse. If the splint rides up and down on the wearer's wrist, it will cause scratching and irritate the wearer. If the material creases or folds, it makes it harder for the wearer to use his or her hand in performing an activity. Many current CMC type splints also employ straps or bands used to secure the splint to the wearer's wrist or to adjust the splint. Besides increasing the bulkiness of the splint, if worn at night, while sleeping, the wearer can unknowingly scratch his or her face, or other parts of their body, by unconsciously rubbing their hand over it. The straps or bands can also snag on clothing causing pulls and rips.

There is currently a need for a CMC splint which is easy and comfortable to wear, is readily put on and taken off, supports use of the hand and thumb for rehabilitation purposes so to provide an orthopedic function, while allowing the hand to be used for a range of other, norm al functions. The splint has a cosmetically pleasing appearance, can be cleaned between wearings, does not snag on the wearer's clothing, and will not scratch the person's skin if they rub the splint against other portions o f their body.

BRIEF SUMMARY OF THE INVENTION

In accordance with the invention, a CMC splint includes a sleeve open at one end to fit over the wearer's hand and extend some distance up their arm. The other end of the sleeve has spaced openings allowing the fingers of the hand to be inserted through this end of the sleeve. A curved pad or stiffening member fits in the glove between the wearer's thumb and index finger. The pad is sufficiently rigid to keep the thumb and index finger spread apart from each other, while still allowing use of the hand for rehabilitation purposes and other normal activities the wearer performs. The sleeve is of a relatively thin, lightweight, skin colored material that is easy to put on and remove, and is washable. No straps are required to hold the splint in place, and the splint fits underneath the sleeve or a shirt or coat. When worn, the splint will not snag the person's clothing. Importantly, use of the splint aids healing of a CMC joint condition.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

Figure 1:
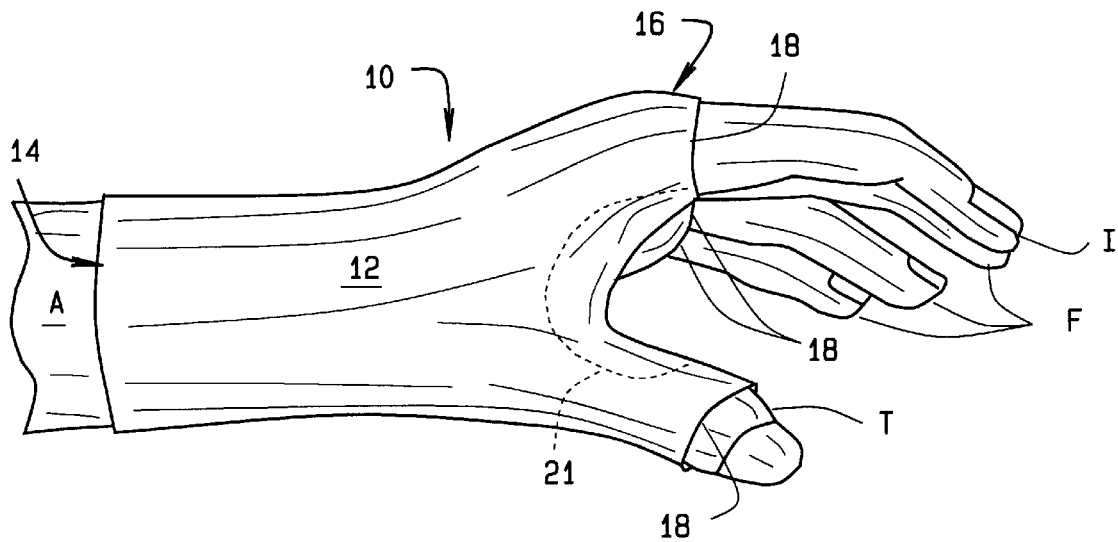
FIG. 1 is a perspective view of a first embodiment of a CMC splint of the present invention.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Referring to the drawings, a CMC splint 10 of the present invention is designed and constructed to support the thumb T and index finger I of a person's hand in a spread apart, separated position. While it important to keep the thumb and index finger separated in order not to aggravate the condition of the CMC joint, it is also important to allow limited motion of the thumb and index finger relative to each other, in order for the person to be able to perform various tasks associated with rehabilitation of their hand, and to perform certain, limited tasks important to carry out their normal day-to-day activities.

Unlike previous splints requiring straps or buckles to secure the splint in place on the wearer's wrist, a sleeve 12 of splint 10 comprises a thin, soft, pliable and washable material having an open, upper end 14 sized to fit over the person's arm A. The material can be skin colored so to have a pleasing cosmetic appearance. This allows the splint to be unobtrusive when being worn. It may also be elasticized for a snug, yet comfortable fit. Since the material is not bulky the splint will fits under the sleeve of a shirt or blouse, or coat or jacket. Finally, the material is washable so the splint can be cleaned between wearings by hand washing with soap and water or in a washing machine using an appropriate detergent.

The splint is constructed so that it is easy to put on and remove and the wearer can do so readily and without assistance from another. The overall length of sleeve 12 is such that it extends a short distance up the wearer's lower arm above their wrist. The sleeve is formed so its upper end 14 fits comfortably, but snugly, over the wearer's arm. The other end 16 of sleeve 12 has a series of spaced openings 18 formed in it. These openings are sized for the wearer's thumb T, index finger I, and other fingers F to extend through this end of the sleeve. As shown in the drawings, the openings 18 for the fingers (including the index finger) allow the fingers to fit through the splint up to their bases. However, the side of the splint through which the thumb fits extends partway along the length of the thumb, covering the thumb up to its first joint.

A thin, generally wedge shaped stiffening member or pad 20 fits into end 16 of sleeve 12. When the splint is being made, a pocket 21 is formed in end 16. After pad 20 is inserted in the pocket, the outer edges of the pocket are sewn or glued together to capture pad 20 in place. The pad is contoured so to fit the web of the hand between the thumb and index finger I. The pad is made of a resilient metal, rubber, or plastic material which permits some flexion between the thumb and index finger. However, the material from which the pad is made is also sufficiently hard that the thumb and index finger are kept spread apart from each other, in a spaced relationship, and cannot be brought into contact with each other. This protects the CMC joint of the hand so the condition of the thumb is not further exacerbated, rehabilitation is promoted, and surgery is avoided.

In FIGS. 3A–3D, pad 20 is shown to have a forward curved surface 22. The curvature of this surface generally corresponds to that of the webbed portion of the hand, between the thumb and index finger, when the hand is relaxed and the thumb and index finger are separated from each other. At the side of the pad adjacent the thumb, surface 22 of the pad has thinner wall, curved section 24 which overlays the portion of the thumb extending from the base of the thumb to its first joint. The pad also has a rear, curved surface 26, the curvature of which corresponds to that of the webbed portion of the hand between the thumb and index finger. The thickness of pad 20 can vary, but is generally only so thick as to provide enough material to keep the thumb and finger readily held apart from each other. It will be appreciated by those skilled in the art that the separation means comprised of pad 20 can include interchangeable pads of varying degrees of hardness.

Figure 2:
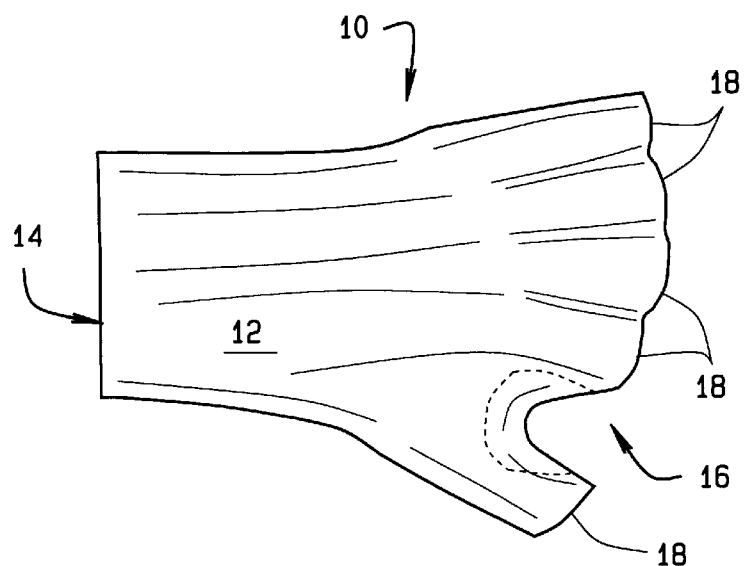
FIG. 2 is top plan view of the splint.
Figure 3A:
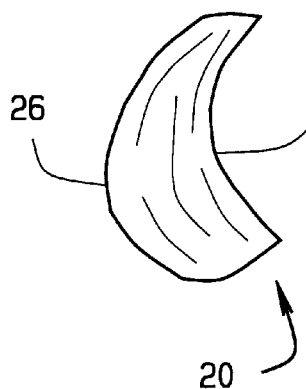
FIGS. 3A–3D are respective top, bottom, front and rear views of a support pad installed in the splint; and, FIG. 4 is a perspective view of a second embodiment of the splint.
Figure 3B:
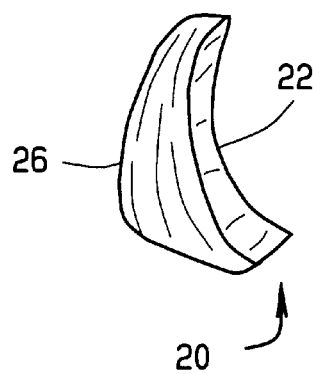
Figure 3C:
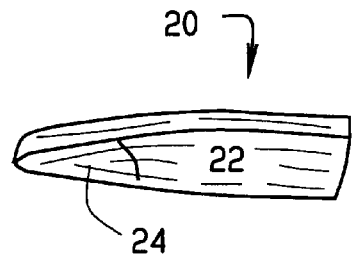
Figure 3D:
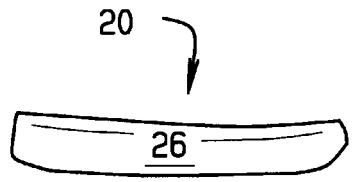
Figure 4:
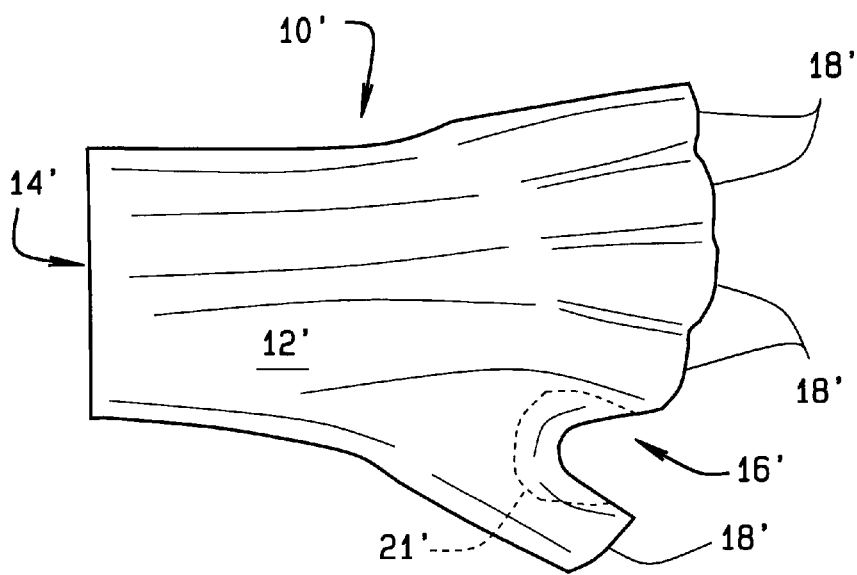

In the embodiment 10' of the splint shown in FIG. 4, the construction of the splint is as previously described. Corresponding reference numerals in FIG. 4 for those shown in FIG. 2 are indicated with a "'". Now, however, pocket 21' is an air pocket. Rather than using a pad 20 to effect separation of the thumb and finger, pocket 21' is a sealed pocket filled with air. The air acts to cushion the thumb and index finger, allowing some slight movement of the two with respect to each other, but keeping them separated. If air is used, the air pressure within the pocket is controllable for wearer comfort.

While not shown in the drawings, other embodiments of the splint effect the cushion provided by pad 20 using a gel or foam injected into the pocket and allowed to set. In these embodiments, the person wears the splint while the material hardens so it properly fits the contour of the hand. A liquid or a granular material may also be used in this regard. Finally, it will be understood that the pad material can be heated prior to the wearer putting on the pad to further promote healing.

In view of the above, it will be seen that the several objects and advantages of the present invention have been achieved and other advantageous results have been obtained.

Having thus described the invention, what is claimed and desired to be secured by Letters Patent is:

1. A CMC splint for supporting the thumb and index finger of a person's hand in a spread apart position comprising:

a sleeve open at one end and sized to fit over the person's hand and up their arm a distance above the person's wrist;

the sleeve being closed at its other end but with openings therein through which the thumb and fingers of the person's hand extend;

separation means contained in the sleeve at the closed end thereof, the separation means acting to keep the person's thumb and index finger spread apart from each other in a spaced relationship to protect the CMC joint and allow the joint to heal, the separation means comprising a pad extending from the base of the index finger, about the curved web portion of the hand separating the index finger and the thumb, and along an inside surface of the thumb a distance above the base of the thumb, the pad being sufficiently stiff so as to not allow the thumb and index finger to be brought together at the base thereof, but sufficiently flexible as to allow limited movement of the thumb and index finger relative to each other; and, a pocket formed in the sleeve in which the pad is inserted.

2. The CMC splint of claim 1 wherein the sleeve has a thumb extension formed at its closed end, the thumb extension extending a distance above the base of the thumb at least so far as the pad extends above the base of the thumb, the extension having an opening in the outer end thereof for insertion of the thumb through the extension.

3. The CMC splint of claim 2 wherein an inner face of the pad is contoured to the sides of the person's thumb and index finger and the curved web portion of the hand separating the thumb and index finger.

4. The CMC splint of claim 1 further including a plurality of similarly formed pads of differing degrees of hardness, the pads being interchangeably fitted into the pocket so to provide differing degrees of protection to the CMC joint.

5. A CMC splint for supporting the thumb and index finger of a person's hand in a spread apart position comprising:

a sleeve open at one end and sized to fit over the person's hand and up their arm a distance above the person's wrist;

the sleeve being closed at its other end but with openings therein through which the thumb and fingers of the person's hand extend; and, separation means contained in the sleeve at the closed end thereof, the separation means acting to keep the person's thumb and index finger spread apart from each other in a spaced relationship to protect the CMC joint and allow the joint to heal, the separation means comprising a curved pocket formed in the sleeve and extending from the base of the index finger, about the curved web portion of the hand separating the index finger and the thumb, and along an inside surface of the thumb a distance above the base of the thumb.

6. The CMC splint of claim 5 wherein the sleeve has a thumb extension formed at its closed end, the thumb extension extending a distance above the base of the thumb at least so far as the pocket extends above the base of the thumb, the extension having an opening in the outer end thereof for insertion of the thumb through the extension.

7. The CMC splint of claim 5 wherein the pocket is air filled.

8. The CMC splint of claim 5 wherein the pocket is filled with a liquid material.

9. The CMC splint of claim 5 wherein the pocket is filled with a granular material.

10. The CMC splint of claim 5 wherein the separation means is a heatable material which is heated to a predetermined temperature prior to the wearer putting on the splint.

* * * * *